United States Patent [19]
Yoshii et al.

[11] Patent Number: 5,856,113
[45] Date of Patent: Jan. 5, 1999

[54] ANTIGEN AND METHOD FOR MEASURING ANTI-ERYTHROCYTE ANTIBODY

[75] Inventors: Haruo Yoshii; Yuriko Fukata, both of Katoh-gun, Japan

[73] Assignee: Nippon Zoki Pharmaceutical Co., Ltd., Osaka, Japan

[21] Appl. No.: 687,778

[22] Filed: Jul. 31, 1996

[30] Foreign Application Priority Data

Aug. 9, 1995 [JP] Japan .................................. 7-225784

[51] Int. Cl.⁶ .................................................. G01N 33/555
[52] U.S. Cl. ........................ 435/7.25; 435/7.95; 436/520
[58] Field of Search ................... 435/7.24, 7.95; 436/520

[56] References Cited

U.S. PATENT DOCUMENTS 5,759,774  6/1998  Hackett et al. .................... 435/7.25
5,773,222  6/1998  Scott .................................. 435/7.25

FOREIGN PATENT DOCUMENTS 1144858  4/1983  Canada .

OTHER PUBLICATIONS

R.M. Dowben, in R.M. Dowben (ED.) *Biological Membranes*, Little–Brown, 1969, pp. 1–2.

J. Koscielak, in C.A. Williams et al (ED), *Methods in Immunology and Immunochemistry*, vol. 1, Academic Press, 1967, pp. 81–83.

J.B. Kwapinski, *Methodology of Immunochemical and Immunological Research*, John Wiley & Sons, 1972, pp. 483–484.

P. Tijssen, *Practice and Theory of Enzyme Immunoassays*, Elsevier Science Publishers BV, 1985, pp. 333–336.

Sodesaki, Japan. Jour. Legal Med. 44 (2), 109–114, 1980.

Huntley et al, Serodiagnosis and Immunotherapy, 1, 455–462, 1987.

*Primary Examiner*—David Saunders
*Attorney, Agent, or Firm*—Fisher, Christen & Sabol

[57] ABSTRACT

Fragments of cell membrane of erythrocyte are used as an antigen for insolubilization in enzyme immunoassay to provide a highly sensitive, excellent quantitative method for measuring anti-erythrocyte antibody. The cell membrane fragments of erythrocyte are the residual membrane fraction after removal of soluble cytoplasm proteins which interfere with the absorbance analysis of enzyme-linked immunosorbent assay (ELISA). The cell membrane fragments of erythrocyte which are used as an antigen may be prepared by destroying the erythrocytes to obtain a cell membrane fragment fraction and a cytoplasm protein fraction. The two fractions may be separated or fractionated by gel filtration, ultrafiltration or centrifugation to isolate the cell membrane fragment fraction. A solution of the cell membrane fragments of erythrocyte is substantially transparent and is useful as an insolubilized antigen for ELISA. The antigen is shelf stable for extended periods when stored in a cool, dark location. An antigen which consists of erythrocyte membrane fragments can be prepared by simple operations and, therefore, it is possible to easily obtain large quantities of antigen for insolubilization.

14 Claims, 2 Drawing Sheets

ANTIGEN AND METHOD FOR MEASURING ANTI-ERYTHROCYTE ANTIBODY

FIELD OF THE INVENTION

The present invention relates to an antigen for enzyme immunoassay consisting of membrane fragments of erythrocytes and also to a method of enzyme immunoassay for anti-erythrocyte antibody utilizing the antigen.

BACKGROUND OF THE INVENTION

A frequently used test system for developing drugs which control the immune system, such as immunosuppressive agents and immunopotentiators, and also for monitoring changes of the immune system, utilizes antibody production by animals as an index. In one method, erythrocyte is used as an antigen for inducing the antibody production. Erythrocytes of horse and sheep have been sold as a reagent since they are available in large quantities. Among them, sheep erythrocyte (sheep red blood cell: SRBC) is most widely used as an antigenic erythrocyte especially because of its easy storage and handling. In "Seikagaku Jiten (Dictionary of Biochemistry)" (second edition; published by Tokyo Kagaku Dojin), SRBC is explained as an independent lemma whereby it is apparent that SRBC has been widely used.

SRBC as an antigen can easily induce antibody production and cellular immunity by its sole administration without mixing with adjuvants (immunopotentiating substances) and, accordingly, it has been widely used, for example, in immunopharmacological and immunotoxicological studies. As a method of measuring anti-SRBC antibody in blood, a classic method utilizing agglutination is used mostly as a practical measuring method. However, the method has disadvantages in that it is discontinuous and is poor in terms of fine quantitativeness. Another disadvantage is the agglutination is confirmed by the naked eye, so there is no objectivity in the method. Accordingly, various attempts have been made for an objective and more quantitative measuring method, i.e. a method of measuring the anti-SRBC antibody by means of enzyme immunoassay (ELISA). However, the methods which utilize enzyme immunoassay up to now still have some problems to be solved, and are not very accurate, easy and convenient.

For example, a method by Mori et al. [hit. J. Immunopharmac., Vol. 11, 597–606 (1989)] is a method in which SRBC per se is used as a granule antigen and is directly insolubilized on a plate by a special means. However, turbidity is poor and, moreover, the red color of erythrocytes remains in an insolubilized antigen. Therefore, the Mori, et al. method is not suitable for ELISA wherein the reaction product is measured by means of absorbance using a marker enzyme. In addition, there is a problem with the reproducibility of the Mori, et al. method.

There are other methods such as a method by Temple et al. [Fundam. Appl. Toxicol., Vol. 21, 412–419 (1993)] and a method by Van Loveren et al. [Int. J. Immunopharmac., Vol. 13, 689–695 (1991)] in which membrane protein of SRBC is solubilized under a specific condition and said soluble protein is used as an antigen for insolubilization. In the method of Van Loveren et al, membrane protein is solubilized by treating with potassium chloride of a high concentration. The substance which is used in those methods is thought to be a part of membrane protein which is solubilized. A problem still remains with respect to the difference in antigenicity between such partial membrane protein and the original SRBC. In addition, the solubilizing and separating operations require time and are troublesome. As such, no suitable insolubilized antigen is used in the methods which have been reported up to now and various problems remain for their practical application.

The present invention provides an enzyme immunoassay for anti-erythrocyte antibody which is objective, reproducible, practical, has excellent quantitativeness and may be performed continuously. The reaction product may be measured by means of absorbance using a marker enzyme. The present invention also provides an antigen for use in enzyme immunoassay which is insolubilized on a plate, has excellent transparency and essentially no turbidity. The antigen does not present the problem of a difference in antigenicity. It is shelf stable for extended periods of time when stored in a dark, cool environment.

SUMMARY OF THE INVENTION

A highly sensitive, quantitative method for measuring anti-erythrocyte antibody is achieved by using fragments of cell membrane of erythrocyte as an antigen for insolubilization in an enzyme immunoassay. The cell membrane fragments are obtained by destroying erythrocytes and removing soluble cytoplasm proteins which interfere with absorbance analysis. The erythrocytes may be destroyed by hemolytic destruction, freeze-and-thawing, or ultrasonic treatment, or combinations thereof. The membrane fragments of erythrocyte may be recovered from, isolated from, or separated from a soluble cytoplasm protein fraction by gel filtration, ultra filtration, or centrifugation. In embodiments of the present invention, the molecular weight of the membrane fragments of erythrocyte is greater than 4,000,000. Use of the cell membrane fragments of erythrocyte in the substantial absence of soluble cell cytoplasm protein provides a measuring system where absorbance increases depending upon the antigen concentration.

In embodiments of the invention, anti-erythrocyte antibody is quantitatively measured by subjecting it to enzyme immunoassay using the cell membrane fragments of erythrocyte as an antigen wherein the fragments are insolubilized in microfiter wells of a 96-well plate. The anti-erythrocyte antibody is added to the well for reaction with the cell membrane fragments. An anti-isotype antibody which is conjugated to an enzyme may be added to the well to bind to the anti-erythrocyte antibody. A substrate for the enzyme may be added to the well to obtain a colored reaction product which may be quantitatively measured by absorbance with a spectrophotometric plate reader.

An aqueous-based buffered solution of the cell membrane fragments of erythrocyte is substantially transparent and accordingly is highly useful as an insolubilized antigen for enzyme-linked immunosorbent assay (ELISA). The antigen of the present invention consisting of membrane fragments of erythrocyte can be stored in a cool, dark location as a buffered solution for extended periods of time of at least about ten months without substantial deterioration of effectiveness.

DETAILED DESCRIPTION OF THE INVENTION

Figure 1:
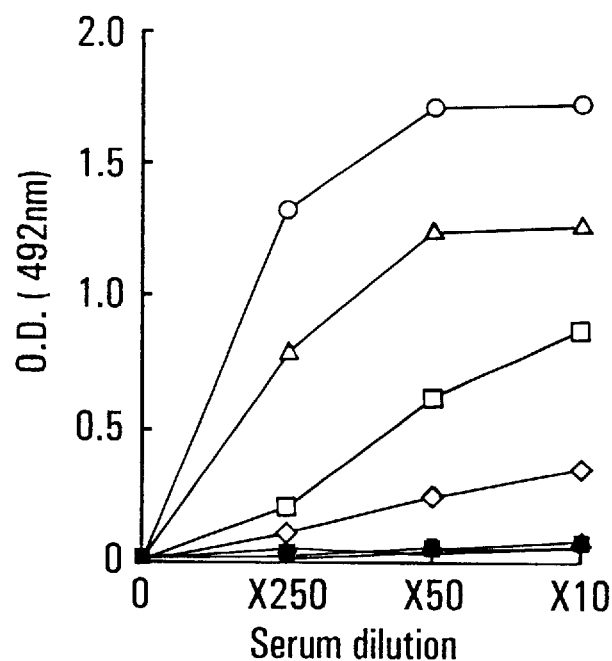
FIG. 1 is an example of the result of ELISA which was conducted using the antigen of the present invention consisting of erythrocyte cell membrane fragments.

The present invention provides an antigen for enzyme immunoassay consisting of membrane fragments of erythrocytes. An enzyme immunoassay of anti-erythrocyte antibody using the antigen is also provided by the present invention. More particularly, the present invention concerns an antigen for enzyme immunoassay consisting of cell membrane fragments which are obtained by destruction of erythrocyte so as not to contain soluble cell cytoplasm protein such as hemoglobin. Antigen may be used for enzyme immunoassay (ELISA) using absorbance analysis without interference from soluble components of cell membranes. The absorbance analysis may be conducted using a spectrophotometric plate reader.

In accordance with the present invention, fragments of cell membrane of erythrocyte are used as an antigen for insolubilization wherein said cell membrane fragments of erythrocyte are the residual membrane fraction after removing the soluble cytoplasm proteins, such as hemoglobin, which interfere with the absorbance analysis of ELISA. The cell membrane fragments of erythrocyte wherefrom cytoplasm proteins such as hemoglobin are removed can be prepared by destroying the erythrocytes followed by subjecting the soluble cytoplasm proteins and membrane components to a fractionation.

In destroying the erythrocyte, known means such as hemolytic destruction, freezing-and-thawing, and ultrasonic treatment, or combinations thereof may be applied. For example, the hemolytic destruction can be easily conducted by a simple operation of exposing the erythrocyte to a hypotonic solution, such as water, and is easy to apply.

Then, with respect to a method of separating soluble cytoplasm protein, such as hemoglobin, and cell membrane fragments, known means such as gel filtration, ultrafiltration and centrifugation may be applied. For example, in the case of gel filtration, it is enough to roughly separate into two fractions: (1) cell membrane fragments having high molecular weight, and (2) other soluble cytoplasm proteins having low molecular weight. When a carrier exhibiting a suitable fractionating coverage is used, only cell membrane fragments can be eluted to a void volume part and can be easily separated from soluble cytoplasm protein fractions with low molecular weights which are is eluted later whereby the antigen of the present invention is able to be prepared by simple operations.

The antigen of the present invention (cell membrane fragments of erythrocyte) obtained by separation from the soluble cytoplasm protein fractions of erythrocyte as such is insolubilized in a plate for enzyme immunoassay whereupon a conventional ELISA can be carried out. With respect to the technique for ELISA such as the antigen insolubilizing method, blocking method, kind of enzyme marking, selection of the substrates, the conditions for enzymatic reaction, and final measuring method, conventional known art may be utilized. Such techniques are mentioned in detail, for example, in *Koso Men-eki Sokuteiho* (*Enzyme Immunoassay*) third edition, edited by Ishikawa, Kawai and Miyai, published by Igaku Shoin, (May 1987), and Kuby, Janis, *Immunology* published by W. H. Freeman and Co., pages 126, 135, and 145–146 (1992), herein incorporated by reference, and other references.

An erythrocyte from any species of animal can be used to prepare the antigen of the present invention. The erythrocyte species chosen may depend upon its availability, antigenicity and the animal species used in the test for antibody production, etc. Usually, SRBC which has been widely used in this field is employed.

The present invention will be illustrated by way of the following examples wherein all temperatures are in °C., all pressures are atmospheric, and all parts, percentages, and ratios are by weight unless otherwise indicated:

EXAMPLE 1

Fractionation of SRBC Membrane Fragments by Gel Filtration

To 1.0 ml of pellets of SRBC was added the same amount (1.0 ml) of distilled water to hemolyze the SRBC. A portion of each mixture was applied to a column of Sepharose CL-6B (manufactured by Pharmacia; 25 mm×69 mm) equilibrated with 0.1M carbonate buffer (pH 9.5), and a gel filtration was conducted under the fractionating condition of 3.0 ml/tube at 4° C. Eluted fractions were measured at an absorbance of 280 nm whereupon two peaks were noted: (1) a small peak (fractions 28–31) corresponding to the void volume, and (2) a peak (fractions 56–67) presumably containing soluble cytoplasm protein coinciding with the peak of hemoglobin. Then the peak of the void volume part and the peak eluted thereafter were each pooled as a cell membrane fragment fraction and a cytoplasm protein fraction, respectively and used as insolubilized antigen in the ELISA of Example 2.

EXAMPLE 2

Measurement of Anti-SRBC Antibody in ELISA

In this example, the cell membrane fraction of the present invention and the cytoplasm protein fraction, each prepared in Example 1, were used to measure anti-SRBC antibody using ELISA in a positive control serum and in a negative control serum.

To prepare the positive control serum, SRBC (0.2 ml) wherein the concentration was adjusted to $5 \times 10^9$ erythrocytes/ml using a physiological saline solution was administered to BALB/c mice intraperitoneally. Serum on the fifth and sixth days after the administration was pooled to give a positive control serum. The serum of normal BALB/c mice was pooled to give a negative control serum.

Both fractions obtained in Example 1 were diluted with a 0.1M carbonate buffer (pH 9.5) to adjust the concentration of protein to obtain samples having a protein concentration in the range of 3–1,00 μg/ml (based upon the absorbance at 280 nm). Each of the fraction solutions (100 μl) was added to each well of a plate for conducting ELISA having 96 wells and insolubilized at 4° C. overnight. Then 200 μl of a phosphate buffer containing 0.1% gelatin (G-PBS) was added thereto followed by blocking at room temperature for one hour. The contents of each well was washed three times with a phosphate buffer containing 0.05% of Tween 20 (T-PBS). Then 100 μl of the positive or negative control serum diluted with G-PBS was added to each of the wells and a reaction was conducted at room temperature for two hours. The contents of each well was washed three times with T-PBS, then 100 μl of anti-mouse IgG (immunoglobulin G) marked with horse radish peroxidase diluted to an extent of 500-fold with G-PBS was added thereto, and the reaction was conducted at room temperature for two hours. The contents of each well was again washed with T-PBS three times, then 100 μl of a coloring solution (prepared by adding 10 mg of o-phenylenediamine dihydrochloride and 10 μl of 33% hydrogen peroxide to 10 ml of a citrate buffer [pH 4.5]) was added and the reaction was conducted at room temperature for 5–10 minutes. The reaction was stopped with 100 μl of 1N hydrochloric acid and the absorbance at 492 nm was measured. An example of the results of the ELISA using the cell membrane fragment fraction as an antigen for insolubilization is given in FIG. 1. The result of the case where the cytoplasm protein fraction was used as an antigen for insolubilization is given in FIG. 2.

Figure 2:
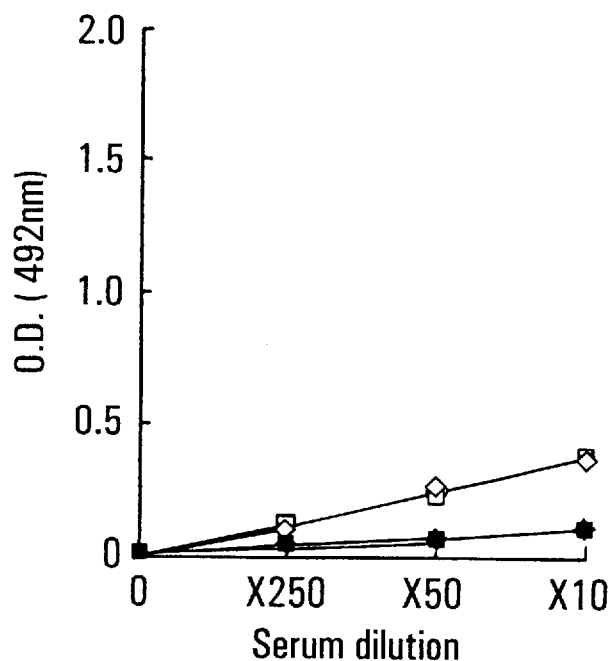
FIG. 2 is an example of the results obtained when cytoplasm protein fractions of erythrocyte was used as an immobilized antigen.

As shown in FIG. 1 and FIG. 2, when anti-SRBC-IgG antibody in the positive is control serum wherein antibody production was induced was used, the absorbance increased depending upon the antigen concentration in the measuring system of the present invention using the cell membrane fragment fraction of erythrocytes as an insolubilized antigen in ELISA. However, in the system where cytoplasm protein fraction is used as an insolubilized antigen, there was no concentration-dependency at all and the anti-SRBC-IgG antibody was not measured quantitatively for the positive control serum. As expected for both fractions, antibody was not measured in the serum in the negative control serum which was serum of normal mice.

Sepharose CL-6B was used as a carrier in the fractionation by gel filtration in Example 1. This carrier for the gel filtration is a globular protein and its fractionating range in terms of molecular weight is from 10,000 to 4,000,000. Accordingly, the molecular weight of the membrane fragment obtained by destruction of erythrocyte is supposed to be more than 4,000,000. However, it is possible to utilize any kind of carrier provided that such a carrier is capable of separating erythrocyte membrane fragment and cytoplasm proteins. It is also possible to utilize any other separation method capable of separating the erythrocyte membrane fragment fraction from the cytoplasm proteins, such as ultrafiltration and centrifugation.

In ELISA, turbidity and degree of coloration of the insolubized antigen have a big influence on the accuracy of the measurement. A solution of cell membrane fragments of erythrocyte which is an antigen of the present invention is almost transparent and is very useful as an insolubilized antigen for ELISA. Since the antigen of the present invention can be prepared by very simple operations as mentioned above, it is possible to provide large quantities of antigen for insolubilization at one time. In addition, the resulting antigen of the present invention consisting of membrane fragments of erythrocyte can be stored in a cool (e.g. 4° C.) and dark place after preparing it into a solution in a phosphate buffer. Even after the antigen solution is stored for ten months for example, measurement is still possible in the same manner as in the initial prepared stage. Therefore, the antigen of the present invention consisting of the erythrocyte membrane fragment and the measuring method using it are very practical.

Further, when compared with the method of Temple et al. or Van Loveren et al. discussed above, wherein a part of solubilized membrane protein of erythrocyte is used, the measuring method utilizing the antigen of the present invention is able to measure the amount of antibody more accurately from an immunological viewpoint. The present invention involves simple operations, is rapid and inexpensive but provides an enzyme immunoassay of anti-erythrocyte antibody having accuracy, high sensitivity and excellent quantitativeness.

We claim:

1. An enzyme immunoassay of anti-erythrocyte antibody, said immunoassay comprising reacting a sample with an insolubilized antigen consisting of an enzyme immunoassay plate and cell membrane fragments of erythrocytes coated thereon in the substantial absence of soluble cell cytoplasm protein, said fragments having been separated from soluble cell cytoplasm protein and then insolubilized in said plate prior to said reacting.

2. A method for measuring anti-erythrocyte antibody comprising subjecting anti-erythrocyte antibody to an enzyme immunoassay using an insolubilized antigen consisting of an enzyme immunoassay plate and cell membrane fragments of erythrocytes coated thereon, said antigen being obtained by: destroying erythrocytes to form a destruction product comprising an erythrocyte cell membrane fragment fraction and soluble cytoplasm proteins; removing soluble cytoplasm proteins which interfere with absorbance analysis, from said destruction product, to form an antigen consisting of said cell membrane fragment fraction in the substantial absence of cytoplasm proteins which interfere with absorbance analysis, said fraction being insolubilized in said enzyme immunoassay plate.

3. A method as claimed in claim 2 wherein said soluble cytoplasm proteins comprise hemoglobin.

4. A method as claimed in claim 2 wherein the cell membrane fragments are insolubilized in a well, the anti-erythrocyte antibody is added to the well for reaction with the cell membrane fragments, an anti-isotype antibody conjugated to an enzyme is added to the well to bind to the anti-erythrocyte antibody, a substrate for the enzyme is added to the well to obtain a colored reaction product, and the colored reaction product is quantitatively measured by absorbance.

5. A method as claimed in claim 2 wherein the soluble cytoplasm proteins are removed from the cell destruction product by gel filtration.

6. A method as claimed in claim 2 wherein the cell membrane fragments are cell membrane fragments of sheep erythrocytes.

7. A method as claimed in claim 2 wherein the cell membrane fragments have molecular weights of greater than 4,000,000.

8. A plate for an enzyme immunoassay of anti-erythrocyte antibody, consisting of an insolubilized antigen consisting of an enzyme immunoassay plate and membrane fragments of erythrocytes coated thereon which have been separated from soluble cell cytoplasm protein.

9. A plate for an enzyme immunoassay of anti-erythrocyte antibody, consisting of an insolubilized antigen consisting of an enzyme immunoassay plate and membrane fragments of erythrocytes coated thereon which have been obtained by destroying erythrocytes and removing soluble cytoplasm proteins, which interfere with absorbance analysis, from said cell membrane fragments.

10. A plate as claimed in claim 9 wherein said soluble cytoplasm proteins comprise hemoglobin.

11. A plate as claimed in claim 9 wherein the cell membrane fragments are insolubilized in a well, the anti-erythrocyte antibody is added to the well for reaction with the cell membrane fragments, and an anti-isotype antibody conjugated to an enzyme is added to the well to bind to the anti-erythrocyte antibody.

12. A plate as claimed in claim 9 wherein the soluble cytoplasm proteins have been removed by gel filtration from the cell membrane fragments prior to being insolubilized.

13. A plate as claimed in claim 9 wherein the cell membrane fragments are cell membrane fragments of sheep erythrocytes.

14. A plate as claimed in claim 9 wherein the cell membrane fragments have molecular weights greater than 4,000,000.

* * * * *